(12) United States Patent
Bains et al.

(10) Patent No.: US 7,070,737 B2
(45) Date of Patent: *Jul. 4, 2006

(54) DISINFECTING ARTICLE WITH EXTENDED EFFICACY

(75) Inventors: Surinder K. Bains, Pleasanton, CA (US); Vincent N. Demaso, Pleasanton, CA (US); William Ouellette, Pleasanton, CA (US)

(73) Assignee: The Clorox Company, Oakland, CA (US)

( * ) Notice: Subject to any disclaimer, the term of this patent is extended or adjusted under 35 U.S.C. 154(b) by 6 days.

This patent is subject to a terminal disclaimer.

(21) Appl. No.: 10/632,573

(22) Filed: Aug. 1, 2003

(65) Prior Publication Data

US 2005/0047961 A1   Mar. 3, 2005

(51) Int. Cl.
*A61L 2/00* (2006.01)
*A01N 59/08* (2006.01)

(52) U.S. Cl. .............................. 422/37; 422/1; 422/40; 422/292; 424/443; 424/661

(58) Field of Classification Search ............... 422/1, 422/37, 40, 292; 424/404, 402, 661, 443; 428/198
See application file for complete search history.

(56) References Cited

U.S. PATENT DOCUMENTS

| 4,833,003 A | * | 5/1989 | Win et al. ................. 428/198 |
| 4,998,984 A | | 3/1991 | McClendon ............... 206/205 |
| 5,087,450 A | | 2/1992 | Lister ........................ 424/402 |
| 5,811,113 A | | 9/1998 | Dorr et al. ................. 424/404 |
| 5,985,302 A | | 11/1999 | Dorr et al. ................. 424/404 |
| 6,231,747 B1 | | 5/2001 | Fukuzuka et al. .......... 205/500 |
| 6,313,049 B1 | | 11/2001 | Heady et al. ............... 442/123 |
| 6,387,384 B1 | | 5/2002 | Probert et al. ............. 424/404 |

FOREIGN PATENT DOCUMENTS

| WO | WO 99/52360 | 10/1999 |
| WO | WO 01/92622 A1 * | 12/2001 |

* cited by examiner

*Primary Examiner*—Krisanne Jastrzab
(74) *Attorney, Agent, or Firm*—David Peterson (57) ABSTRACT

The present invention relates to disinfecting articles and wipes saturated with an aqueous hypohalite composition with improved stability and extended efficacy for cleaning and disinfecting surfaces against harmful and infectious pathogens. The wipe substrate is selected from hypohalite stable materials that do not catalyze decomposition of the associated aqueous hypohalite releasing compositions. The disinfectant articles provide a minimum disinfecting level of active hypohalite for an extended time, ensuring reliably disinfection of hard surfaces such as countertops, toilet seats, door knobs and the like commonly found in the home, hospital, food service and other industries.

26 Claims, 1 Drawing Sheet

Fig. 1

DISINFECTING ARTICLE WITH EXTENDED EFFICACY

FIELD OF THE INVENTION

The present invention relates to disinfecting articles providing effective cleaning and antimicrobial treatment of microbiologically contaminated surfaces. More particularly, it relates to the use of aqueous hypohalite compositions associated with a hypohalite stable and hypohalite non-degrading absorbent substrate that preserves the antimicrobial efficacy of the disinfectant article over representative storage times and/or storage conditions. The wipe substrate is selected from hypohalite stable materials that do not catalyze decomposition of the associated aqueous hypohalite compositions.

BACKGROUND OF THE INVENTION

There is a need for a stable cleaning and disinfecting wipe and article that is capable of cleaning and removing residues from soiled surfaces while simultaneously destroying undesirable microorganisms, e.g. bacteria, mold, viruses, prions and the like that colonize on common surfaces with which people come into contact, such as doorknobs, countertops, toilet seats, floors, beds, walls, and the like.

Hypohalite releasing compounds, such as the hypohalites and related compounds that release active forms of hypohalite and/or halogens, are extremely effective disinfectants capable of destroying a wide range of microorganisms. Hypohalite releasing antimicrobial compounds, and in particular the hypohalites, constitute a class of strong chemical oxidants possessing both cleaning and bleaching properties in addition to their antimicrobial properties making them superior to other disinfectants, such as quaternary ammonium biocides. The hypohalite class of chemical oxidants act to rapidly oxidize susceptible substances found in inorganic, organic and biological materials, rendering them more easily removed from surfaces, and in the case of colored or pigmented materials, bleaching them to white or colorless end products resulting in effective cleaning and stain removal from soiled surfaces. Owing to their strong oxidizing capability, hypohalites also possess inherent disinfection properties and additionally possess desirable characteristics including excellent aqueous solubility, mobility and a highly dissociative ionic nature. A further advantage of the hypohalite class with regard to disinfectancy, is the speed and efficacy with which they attack microorganisms and either destroy them or render them non-viable following very short contact times. Yet a further advantage of the hypohalites is the wide susceptibility of many different types of microbial pests to their strong oxidizing potential and essentially the absence of any known microbe to develop an effective resistance against the action of these materials.

Typically, microbiologically contaminated surfaces seldom comprise only the microorganisms themselves, but include the presence of soils and other residues, including organic, inorganic and biological residues associated with the source of the microbiological contamination. These residues, including, for example, saliva, bodily fluids, blood and common soils such as foods, oils and dirt, not only host microorganisms, but can act to shield and protect the microorganisms from the disinfectant action of non-hypohalite disinfectant materials.

One seeming disadvantage of the hypohalite class of materials is their susceptibility to decomposition, including self-decomposition and reactive decomposition owing to the interaction of the hypohalites with the substrates and materials in which they come into contact during storage, such as packaging materials, and particularly in the case of pre-wetted wipes, the material used as the absorbent carrier substrate which is impregnated with the disinfectant composition. Hence, freshly prepared solutions or disinfectant articles utilizing these materials are typically required to ensure adequate activity for ensuring effective disinfection of surfaces. Attempts have been made in the past to provide a convenient disinfectant article by absorbing a hypohalite solution onto an absorbent towel or carrier. However, prior attempts have failed to produce a hypohalite releasing disinfectant wipe with sufficient stability to ensure suitable disinfecting efficacy at time of use, particularly following typical storage times and/or less than ideal storage conditions representative of real world environments encountered in the home, office, business, hospital or field where needed.

U.S. Pat. No. 4,998,984, to McClendon, describes a premoistened disinfectant article impregnated with a disinfectant composition that may include sodium hypochlorite and is prepackaged in a liquid impermeable container. U.S. Pat. No. 5,087,450, to Lister, describes a viral wipe to remove organic material having viral contaminants from a surface which consists of a porous gauze pad lined with a non-porous flexible fluid impervious barrier layer fused to one side and impregnated with 10% sodium hypochlorite and stored in a protective foil, plastic and paper layered package. Lister notes that the 10% sodium hypochlorite solution becomes unstable within a short period of time.

U.S. Pat. No. 5,985,302, to Dorr, et al., describes a method for inactivating HIV infected blood which involves first swabbing a contaminated surface with a first aqueous calcium and/or sodium hypochlorite impregnated fibrous towlette, followed by a second swabbing with a second towlette impregnated with a neutralizing sodium thiosulfate solution. However, the Dorr et al. example exhibits poor stability and complete loss of inactivating activity even of a dry calcium hypochlorite/methyl cellulose system freshly dissolved in water to produce a disinfecting solution after only 10 days storage at 50° C. U.S. Pat. No. 6,313,049, to Heady and Wolkensperg, describes a pre-packaged fabric-saturated absorbent sheet with the U.S. food-industry legal chlorine disinfectant solution and discloses the use of cotton, paper or sponge sheets as absorbents. U.S. Pat. No. 6,387,384, to Probert and Probert, describes a prepackaged towlette bearing sodium hypochlorite and discloses the use of gauze or bandage material as absorbents.

The prior art fails to provide a stable disinfectant article that maintains acceptable stability after representative storage times and storage conditions typical of actual usage conditions encountered in the real world. For instance, most commercial product distribution channels result in products ageing several months following manufacture before being placed on sale, followed by significant delays before actually being used. During this time, products are seldom stored under ideal conditions, but rather are exposed to temperature variations typical of the home, field and industrial environment. Most significantly, the prior art fails to disclose suitable absorbent carrier substrates with acceptable stability nor a reliable means for selecting an appropriate absorbent material suitable for extended stability of aqueous hypohalite disinfectant articles to ensure reliable antimicrobial efficacy when needed.

Clearly, there remains an unmet need for an aqueous hypohalite disinfecting article with improved stability that can provide the required antimicrobial efficacy for disinfecting microbiologically contaminated surfaces, particularly following typical storage times and/or less than ideal storage conditions representative of real world environments encountered in the home, office, business, hospital or field where needed.

SUMMARY OF THE INVENTION

1. In accordance with the above objects and those that will be mentioned and will become apparent below, one embodiment of the invention comprises a disinfecting article comprising:
   a. an aqueous hypohalite releasing composition,
   b. an absorbent carrier, and
   c. a packaging system dispensibly housing a single or multiple number of disinfectant substrates, wherein said disinfectant article maintains the stability of the hypohalite releasing composition of at least 25% after 11 days at 120° F.

2. An additional embodiment of the invention comprises a method of disinfecting hard surfaces comprising treating the hard surface with a disinfecting article comprising:
   a. an aqueous hypohalite releasing composition,
   b. an absorbent carrier, and
   c. a packaging system dispensibly housing a single or multiple number of disinfectant substrates, wherein said disinfectant article maintains the stability of the hypohalite releasing composition of at least 25% after 11 days at 120° F.

3. An additional embodiment of the invention comprises a hypochlorite-containing disinfecting wipe with improved stability that provides superior germ killing on surfaces such as countertops, floors, beds, walls, doorknobs, toilet seats, and the like.

BRIEF DESCRIPTION OF THE DRAWINGS

Further features and advantages will become apparent from the following and more particular description of the preferred embodiments of the invention, as illustrated in the accompanying FIG. 1.

INVENTIVE EXAMPLE 1

Disinfectant wipe with Composition 1 (Table 1) loaded onto a 100% polyester substrate, stored in an upright sealed canister for up to 6 weeks at a temperature of 120° F.

INVENTIVE EXAMPLE 2

Disinfectant with Composition 2 (Table 1) loaded onto an identical 100% polyester substrate and stored as in Example 1 herein.

Comparative Example J

Disinfectant wipe with Composition 1 (Table 1) loaded onto 100% polypropylene substrate following Example J (Table 2), and stored as in Example 1 herein.

Commercial Wipe

Dispatch Hypochlorite Wipes, stored as supplied in individually sealed packages, for up to 3 weeks at a temperature of 120° F.

DETAILED DESCRIPTION OF THE INVENTION

Before describing the present invention in detail, it is to be understood that this invention is not limited to particularly exemplified systems or process parameters as such may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

It must be noted that, as used in this specification and the appended claims, the singular forms "a," "an" and "the" include plural referents unless the content clearly dictates otherwise. Thus, for example, reference to a "surfactant" includes two or more such surfactants.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

The following examples illustrate disinfecting articles and compositions of the described invention. The exemplified compositions are illustrative only and do not limit the scope of the invention. Unless otherwise specified, the proportions in the examples and elsewhere in the specification are by weight percent of the total liquid composition, and loading levels of the example compositions are by unit weight of composition per unit weight of the absorbent carrier matrix and thus expressed as a unit-less weight/weight ratio.

The present invention relates to a disinfecting article and wipe for cleaning and disinfecting surfaces, in which the disinfecting article comprises an aqueous hypohalite releasing composition adsorbed onto a hypohalite stable and hypohalite non-degrading absorbent carrier material. The disinfecting articles comprise:

(a) an aqueous hypohalite releasing composition, and;
(b) an absorbent carrier comprising a substrate that is hypohalite stable and hypohalite non-degrading, that is a substrate that does not catalyze the decomposition of the hypohalite releasing composition, and;
(c) a packaging system dispensibly housing a single or multiple number of disinfectant substrates.

The present invention is directed to hypohalite stable and hypohalite non-degrading absorbent carrier materials for holding and dispensing aqueous antimicrobial hypohalite releasing compositions. The present invention is also directed to stable aqueous hypohalite compositions that are preferably used in association with hypohalite stable and hypohalite non-degrading absorbent carrier materials. The present invention is further directed to a disinfectant article and packaging system such as an upright canister for storing and conveniently dispensing a continuous number of individually dividable wipes on demand, while providing for extended stability and disinfectant efficacy owing to improved stability of the associated hypohalite releasing disinfectant compositions absorbed onto the absorbent carrier materials.

Absorbent Carrier

Suitable absorbent carriers may be provided by a variety of sources, including woven and non-woven webs, fabrics, foams, sponges and similar material constructs capable of absorbing the liquid disinfectant composition of the present invention. Generally, the absorbent carrier is preferred to be in sheet form, that is, in a form in which the cross-sectional thickness dimension of the absorbent carrier is proportionally smaller than either its approximate width or length dimension in order to provide at least one surface whose surface area is sized appropriately with respect to the intended surface to be treated with the disinfectant article. The absorbent carrier may be formed into individual sheets or wipes, or a continuous sheet, preferably with some separation means provided, such as partial tears or perforations across at least one dimension of the sheet, such that the sheet may be subdivided prior to use to a suitable size for the particular need at hand.

The absorbent carrier may consist of a single layer, or multiple layers of one or more materials, or combination of one or more materials and/or one or more forms of materials, wherein multiple layers or multiple forms are bound by a suitable means to each other to prevent separation. For example, a sheet of one material may be combined with a second sheet of a second material, and bound together by a suitable means, such as by adhesion, heat or sonic welding, to prevent their separation. As a further example, a non-woven sheet of one material may be combined with a second material formed into deformable and compressible foam, and bound together by a suitable means. In this manner, all conceivable combinations of materials may be combined to provide useful articles for a variety of cleaning and disinfecting requirements.

Further, the absorbent carrier can be combined with non-absorbent materials, preferably in the form of films, sheets or blocks. Preferably, the non-absorbent materials are liquid impervious, in that they do not permit the passage of the disinfectant compositions of the present invention. In one example, the non-absorbent materials may be bonded to one side of a suitable absorbent carrier in order to provide a liquid impervious barrier to prevent passage of the disinfectant compositions from the absorbent material to the non-bonded surface of the barrier material. One example would be an absorbent material in a thin sheet form bonded with a liquid impervious barrier film in thin sheet form to one side of the absorbent material forming an effective barrier to the disinfectant compositions that would allow the layered disinfectant article to be handled by the user without direct contact with the disinfectant wetted side of the layered article. Another example would be a thin liquid impervious plastic sheet bounded to an absorbent foam, whereby the user would only come into contact with the plastic sheet during use rather than the liquid disinfectant absorbed into the foam that is displaced by pressure applied while wiping the surface to be treated.

According to the present invention, the absorbent carrier may be produced by any method known in the art. For example non-woven material substrates can be formed by dry forming techniques such as air-laying or wet laying such as on a paper-making machine. Other non-woven manufacturing techniques such as hydroentangling, melt blown, spun bonded, needle punched and related methods may also be used. However, the substrate must be made substantially free of binder or latex and other impurities that may degrade or interact with the disinfectant composition. Many manufacturing techniques, such as air-laying, do not lend themselves to the formation of binder- and latex-free absorbent carriers. As such they are not preferred manufacturing techniques. Hydroentrangling manufacturing techniques using high speed water jets are generally preferred due to the high density matrices produced and owing to the high water flow volume the high degree of cleanliness of the resulting non-woven articles produced by this method.

Suitable absorbent carriers are generally selected from man-made and synthetic construction materials or substrates. Suitable construction materials include synthetic polymers. For good cleaning, absorption, handling and loading characteristics, it is desirable that the absorbent carrier materials be in the form of fiber, webs or foams of the suitable construction materials. Suitable forms employing fibers include woven and non-woven structures. Woven structures include meshes, screens, knits, fabrics and other similarly woven structures that are of sufficiently high fiber count and strength to be handled by typical machinery and process equipment needed for forming, cutting and packaging the disinfectant articles, preferably when in a dry state. Suitable structures include those structures that are of sufficiently high fiber count and strength to be dispensed and handled during use, preferably when in a dry state, and more preferably when in a wetted state. Suitable woven and non-woven structures are composed of fibers with both sufficiently fine fiber sizes and fiber densities to provide some absorption capacity and enable loading of a sufficient quantity of the disinfectant solution so as to provide for effective treatment of surfaces. Suitable non-woven structures include those structures that are of sufficiently high fiber count and strength to be dispensed from the packaging articles without significant deformation, tearing or ripping and handled during use without unraveling, abrading or tearing, preferably when in a wetted state.

Absorbent Carrier Substrates

Suitable substrates employed for constructing the absorbent carrier may be provided by a variety of sources, and include all suitable substrate that are hypohalite stable, in that they undergo no significant degradation, that is no significant chemical or physical change in structure, properties or form, owing to contact with the disinfectant compositions employed in the present invention, even after extending contact or storage times under representative storage conditions. Preferred are suitable substrates that do not cause significant degradation of the associated or absorbed disinfecting compositions, that is, substrates that do not catalyze or significantly accelerate the decomposition of the associated hypohalite compositions.

Suitable materials of construction generally include synthetic polymer substrates, such as polyethylene terephthalate (PET), polyester (PE), high density polyethylene (HDPE), polyvinyl chloride (PVC), chlorinated polyvinylidene chloride (CPVC), polyacrylamide (ACAM), polystyrene (PS), polypropylene (PP), polycarbonate (PC), polyaryletherketone (PAEK), poly(cyclohexylene dimethylene cyclohexanedicarboxylate) (PCCE), poly(cyclohexylene dimethylene terephthalate) (PCTA), poly(cyclohexylene dimethylene terephtalate) glycol (PCTG), polyetherimide (PEI), polyethersulfone (PES), poly(ethylene terephthalate) glycol (PETG), polyketone (PK), poly(oxymethylene); polyformaldehyde (POMF), poly(phenylene ether) (PPE), poly(phenylene sulfide) (PPS), poly(phenylene sulfone) (PPSU), syndiotactic polystyrene (syn-PS), polysulfone (PSU), polytetrafluoroethylene (PTFE), polyurethane (PUR), poly(vinylidene fluoride) (PVDF), polyamide thermoplastic elastomer (TPA), polybutylene (PB), polybutylene terephthalate (PBT), polypropylene terephthalate (PPT), polyethylene naphthalate (PEN), polyhydroxyalkanoate (PHA), poly(methyl)methacrylate (PMMA) and polytrimethylene terephthalate (PTT).

Suitable materials of construction also include copolymers made from the following monomers: acrylonitrile-butadiene-styrene (ABS), acrylonitrile-styrene-acrylate (ASA), ethylene-propylene (E/P), ethylene-vinyl acetate (EVAC), methyl methacrylate-acrylonitrile-butadiene-styrene (MABS), methacrylate-butadiene-styrene (MBS), melamine-formaldehyde (MF), melamine-phenol-formaldehyde (MPF), phenol-formaldehyde (PF), styrene-butadiene (SB), styrene-maleic anhydride (SMAH), copolyester thermoplastic elastomer (TPC), olefinic thermoplastic elastomer (TPO), styrenic thermoplastic elastomer (TPS), urethane thermoplastic elastomer (TPU), thermoplastic rubber vulcanisate (TPV), copolymer resins of styrene and acrylonitrile (SAN), styrene butadiene copolymer (SBC) and vinyl acetate-ethylene copolymer (VAE). Preferably, the substrate is selected from the group consisting of polyester, modified polyester, and polyester blends.

The substrate and the absorbent carrier constructed from said substrate herein is substantially free, preferably devoid, of any binders or latex materials. Substantial elimination of binders and latexes, and the like, can be accomplished by pre-washing the dry absorbent carrier in soft, distilled or de-ionized water or other solvents, or by using a process, such as hydroentangling (also known in the art as spunlace technology). More specifically, in the hydroentangling process, a fibrous web is subjected to high-velocity water jets, preferably employing de-ionized, distilled or soft water that entangle the fibers. The non-woven material may then be subjected to conventional drying and wind-up operations, as known to those skilled in the art. Since the hydroentangling process precludes the use of binders, and can be used to wash off fiber latexes, it is the most preferred process to be used in the manufacture of materials of construction of the present invention.

Suitable materials of construction that are readily available in commerce include the SONTARA® brand of non-woven fabrics produced by Dupont. Representative materials include 100% polyester substrate materials designated SONTARA® 8001, 8005H, 8010 and 8061, and 50% polyester/50% Dacron® blends designated SONTARA® 8100 and including hydrophilically modified 100% polyester substrate material designated SONTARA® 8005H. Additional examples include materials commercially available from Polymer Group Inc, including 100% spunlaced polyester materials designated M001, M022, M040X, CG003, CG005, CG2009, M017 and N2006. Representative materials also include spunlaced 100% polyester materials available from Jacob Holms Industries, designated as 350160 and 10203-003.

Absorbency and Loading

The absorbent carrier preferably has a weight of from about 10 $gm^{-2}$ (grams per meter squared) to about 200 $gm^{-2}$. More preferably, the absorbent carrier has a weight of at least about 15 $gm^{-2}$ and more preferably less than about 150 $gm^{-2}$, more preferably the basis weight is in the range of about 20 $gm^{-2}$ to about 120 $gm^{-2}$, and most preferably from about 25 $gm^{-2}$ to about 10 $gm^{-2}$.

In preparing pre-wetted disinfectant articles according to the present invention, the composition is applied to at least one surface of the absorbent carrier material. The composition can be applied at any time during the manufacture of the articles. Preferably the composition can be applied to the absorbent carrier after the absorbent carrier has been dried. Any variety of application methods that evenly distribute disinfecting compositions can be used. Suitable methods include spraying, dipping, or rolling whereby the composition is forced through tubes in contact with the absorbent carrier whilst the absorbent carrier passes across the tube or combinations of these application techniques. For example, spraying the composition on a rotating surface such as calendar roll that then transfers the composition to the surface of the absorbent carrier. The composition can be applied either to one surface of the absorbent carrier or both surfaces, and preferably both surfaces.

The composition can also be applied uniformly or non-uniformly to the surfaces of the absorbent carrier. By non-uniform it is meant that for example, the amount or pattern of distribution of the composition can vary over the surface of the absorbent carrier. For example, some of the surface of the absorbent carrier can have greater or lesser amounts of disinfectant composition, including portions of the surface that do not have any composition on it. Preferably however the composition is uniformly applied to the surfaces of the absorbent carrier, or most preferably to the absorbent surface of the disinfectant article that comprises multiple layers or multiple materials of construction.

Preferably, the composition can be applied to the absorbent carrier at any point after it has been dried. For example, the composition can be applied to the absorbent carrier prior to calendaring or after calendaring and prior to being wound up onto a parent roll. Typically, the application will be carried out on an absorbent carrier unwound from a roll having a width equal to a substantial number of wipes it is intended to produce.

When the absorbent carrier matrix is produced with a bonded liquid impervious layer forming an essentially impervious barrier to one side of the disinfectant article, it is then preferred that application of the disinfectant composition is made to the absorbent side of the article.

Alternatively, the disinfectant composition can also be applied at a later stage in the processing of the disinfectant articles, being applied to the substantially dry absorbent carrier after it has been placed into the respective storage pouch, container, canister or other packaging means, but prior to sealing or closure of said packaging means. In this alternative application means, the disinfectant solution is preferably applied by spraying, dripping or nozzle injection of a metered aliquot of the liquid disinfectant composition directly onto the absorbent material within each open package at a convenient processing stage.

The composition is typically applied in an amount of from about 1 gram to about 10 gram per gram of absorbent carrier, preferably from about 1.5 gram to about 8.5 gram per gram of absorbent carrier, most preferably from about 2 gram to about 5 gram per gram of dry absorbent carrier.

Those skilled in the art will recognize that the exact amount of aqueous composition applied to the absorbent carrier will depend on the basis weight of the absorbent carrier and on the end use of the product. In one preferred embodiment, a relatively low basis weight absorbent carrier, from about 20 $gm^{-2}$ to about 80 $gm^{-2}$ is used in the making of a pre-moistened cleaning and disinfectant wipe suitable for cleaning lightly soiled counters, stove tops, cabinetry, walls, sinks and the like. For such end uses, the dry absorbent carrier is loaded with an aqueous composition of the invention at a factor of from about 2 grams to about 10 grams per gram of dry absorbent carrier. In another preferred embodiment, a higher basis weight absorbent carrier, from about 40 $gm^{-2}$ to about 200 $gm^{-2}$ is used in the making of the pre-moistened disinfectant wipe suitable for cleaning heavily soiled or larger area surfaces, including floors, walls and the like. In such instances, the wipe may further be sold with, or designed to work with, a hand held implement comprising a handle and designed for wiping and cleaning. Examples of such implements are commercially available under the trade names Ready-Mop®, a product of The Clorox Company, and Swiffer®, a product of the Procter and Gamble Company. For such end uses, the dry absorbent carrier is loaded with an aqueous composition of the invention at a factor of from about 2 grams to about 8 grams per gram of dry absorbent carrier.

Disinfectant Compositions

Disinfectant Actives

Suitable hypohalite bleaches may be provided by a variety of sources, including bleaches that lead to the formation of positive halide ions and/or hypohalite ions, as well as bleaches that are organic based sources of halides, such as chloroisocyanurates, haloamines, haloimines, haloimides and haloamides, or mixtures thereof. These bleaches also produce hypohalite-bleaching species in situ. Suitable hypohalite bleaches for use herein include the alkali metal and alkaline earth metal hypochlorites, hypobromites, hypoiodites, chlorinated trisodium phosphate dodecahydrates, potassium and sodium dichloroisocyanurates, potassium and sodium trichlorocyanurates, N-chloroimides, N-chloroamides, N-chlorosulfamide, N-chloroamines, chlorohydantoins such as dichlorodimethyl hydantoin and chlorobromo dimethylhydantoin, or mixtures thereof.

In a preferred embodiment wherein the compositions herein are liquid, said hypohalite bleach is an alkali metal and/or alkaline earth metal hypochlorite, or mixtures thereof. More preferably, for liquid compositions said hypohalite bleach is an alkali metal and/or alkaline earth metal hypochlorite selected from the group consisting of sodium hypochlorite, potassium hypochlorite, magnesium hypochlorite, lithium hypochlorite and calcium hypochlorite, and mixtures thereof. Even more preferably, for liquid compositions said hypohalite bleach is sodium hypochlorite.

The halogen bleach is present in an amount from above zero to about 15 weight percent of the composition and preferably from about 0.001 weight percent (10 ppm) to about 10 weight percent of the composition, and most preferably from about 0.005 (50 ppm) to about 5 weight percent of the composition. A particularly preferred bleach in this invention is sodium hypochlorite, having the chemical formula NaOCl, present in an amount ranging from about 0.001 to about 15 weight percent of the composition, more preferably from about 0.005 (50 ppm) to about 10 weight percent, and most preferably from about 0.005 (50 ppm) to about 5 weight percent of the composition.

Electrolyte/Buffer

The electrolyte/buffer component of the cleaning and disinfecting composition appears to promote a favorable environment of pH and ionic strength in which the hypohalite releasing disinfectant is stabilized against accelerated decomposition and loss of disinfectant efficacy. An electrolyte functions to provide a source of ions (generally anions) in aqueous solution. The electrolyte thus provides a charged medium in which the optional surfactant and/or optional thickeners can associate to provide thickening, or other favorable rheological properties such as shear thinning and/or viscoelastic properties, which provide for thickened compositions that may be readily formulated, mixed and handled by commercial processing equipment and effectively transferred by commercial pumping and dosing equipment for convenient loading onto the absorbent carrier. Suitably thickened and rheologically enhanced disinfecting compositions provide the additional benefit of higher loading capabilities onto their respective absorbent carriers, reduced dripping and evaporation during storage and use. Suitably thickened and rheologically enhanced disinfecting compositions also provide the additional benefit of clinging to treated surfaces, particularly uneven, sloped or vertical surfaces with greater tenacity and resistance from gravity to provide more efficient coverage, effective contact time and overall enhancing the cleaning and disinfectant efficacy of the compositions.

A buffer principally acts to maintain a favorable pH of the associated aqueous disinfectant compositions, particularly when absorbed in intimate contact with the absorbent carrier materials employed. In the present invention, alkaline pH is favored for purposes of maintaining halogen bleach stability. Some compounds will serve as both electrolyte and buffer. These particular electrolyte/buffer compounds are generally various inorganic acids, for example, borates, polyphosphates, pyrophosphates, triphosphates, tetraphosphates, silicates, metasilicates, polysilicates, carbonates, and hydroxides; alkali metal salts of such inorganic acids; and mixtures of same. Certain divalent salts, e.g., alkaline earth salts of phosphates, carbonates, hydroxides, etc., can function singly as buffers. If such a divalent salt compound were used, it would be combined with at least one of the above-mentioned electrolyte/buffer compounds to provide the appropriate pH adjustment. It may also be suitable to use materials such as aluminosilicates (zeolites), borates, aluminates and bleach-stable organic materials, such as the lower C1–C10 alkyl dicarboxylic acids including gluconates, succinates, and maleates, as buffers. Sodium chloride or sodium sulfate can be used as electrolytes, but not buffers, if necessary, to maintain the ionic strength necessary for the desired rheology, if optional surfactants and/or thickeners are employed.

An especially preferred electrolyte/buffer compound is an alkali metal silicate, which is employed in combination with an alkali metal hydroxide to provide effective pH control and can also function as a metal ion sequestrant. The preferred silicate is sodium silicate, which has the empirical formula $NaO:SiO_2$. The ratio of sodium oxide: silicon dioxide is about 1:4 to 1:1, more preferably about 1:2. Silicates are available from numerous sources, such as the PQ Corporation. The electrolyte/buffer compounds function to keep the pH range of the inventive cleaning and disinfecting composition preferably above 7.0, more preferably at between about 10.0 to about 14.0, and most preferably at between about 11.5 and 13.5. The amount of electrolyte/buffer can vary from about 0.01 to about 10 weight percent of the composition, more preferably from about 0.05 to about 5 weight percent of the composition, and most preferably from about 0.05 to about 1.0 weight percent of the composition.

Water

It should be noted that the main ingredient in the inventive compositions is water, preferably softened, distilled or deionized water. Water provides the continuous liquid phase into which the other ingredients are added to be dissolved/dispersed. The amount of water present generally exceeds 90% and, indeed, can be as high as 99.9%, although generally, it is present in a quantity sufficient (q.s.) to take up the remainder of the specially formulated disinfectant compositions of the present invention.

Surfactant

Optionally, a surfactant suitable for use in this invention is selected from anionic, non-ionic, amphoteric, zwitterionic surfactants and mixtures thereof. It is especially preferred to use a combination of anionic and bleach-stable, non-ionic surfactants. The anionic surfactant is selected from bleach-stable surfactants such as alkali metal alkyl sulfates, secondary alkane sulfonates (also referred to as paraffin sulfonates), alkyl diphenyl ether disulfonates, fatty acid soaps, and mixtures thereof. Such an anionic surfactant will preferably have alkyl groups averaging about 8 to about 20 carbon atoms. In practice, any other anionic surfactant that does not degrade chemically when in contact with a hypohalite, e.g., hypochlorite, bleaching species should also work.

An example of a particularly preferred secondary alkane sulfonate is HOSTAPUR SAS, manufactured by Farbwerke Hoechst A. G., Frankfurt, West Germany. Examples of typical alkali metal salts of alkyl benzene sulfonic acids are those manufactured by Pilot Chemical Company sold under the trademark CALSOFT. An example of a typical alkali metal alkyl sulfate is CONCO SULFATE WR, sold by Continental Chemical Company, which has an alkyl group of about 16 carbon atoms. When the electrolyte used is an alkali metal silicate, it is most preferable to include a soluble alkali metal soap of a fatty acid, such as a hexyl to tetradecyl fatty acid soaps. Especially preferred are sodium and potassium soaps of lauric and myristic acid. When used as a component of the inventive cleaning composition, the alkali metal soap of a fatty acid is present in an amount from above zero to about 10 weight percent of the composition.

Examples of preferred bleach-stable, non-ionic surfactants are amine oxides, especially trialkyl amine oxides, as represented in the formula expression RR'R"NO, in which R' and R" may be alkyls of 1 to 3 carbon atoms and are most preferably methyls, and R is an alkyl of about 10 to 20 carbon atoms. When R' and R" are both methyl and R is alkyl averaging about 12 carbon atoms, the structure for dimethyldodecylamine oxide, a particularly preferred amine oxide, is obtained. Representative examples of these particular types of bleach-stable, non-ionic surfactants include the dimethyldodecylamine oxides sold under the trademark AMMONYX LO by Stepan Chemical. Yet other preferred amine oxides are those sold under the trademark BARLOX by Lonza, CONCO XA sold by Continental Chemical Company, AROMAX sold by Akzo, and SCHERCAMOX, sold by Scher Brothers, Inc. These amine oxides preferably have main alkyl chain groups averaging about 10 to about 20 carbon atoms.

Other types of suitable surfactants include amphoteric surfactants such as, for example, betaines, imidazolines and certain quaternary phosphonium and tertiary sulfonium compounds.

It is suitable to use one or more surfactants in the inventive compositions. In the inventive composition, total surfactant, when present, is included in an amount ranging from about 0.001 to about 20 weight percent of the composition, preferably in an amount ranging from about 0.01 to about 5 weight percent of the composition. For reduced surface residue and to decrease the tendency of the compositions to contribute to excess foaming, residual filming or streaking, and particularly for use on glossy or shiny surfaces, total surfactant present is most preferably from about 0.01 to about 1.0 weight percent of the composition, when included.

Secondary Surfactant and Hydrotropes

Optionally, an additional co-surfactant may be added to the disinfectant composition of this invention. Preferred materials include the bleach stable anionic surfactants and hydrotropes. The bleach stable anionic surfactants include alkali metal alkyl sulfates, alkylarylsulfonates, primary and secondary alkane sulfonates (also referred to as paraffin sulfonates), alkyl diphenyloxide disulfonates, and mixtures thereof. The anionic surfactants will have alkyl groups preferably averaging about 8 to 20 carbon atoms. The alkyl arylsulfonic acid salts of preference are linear alkylbenzene sulfonates, known as LAS's. Typical LAS's have C8–16 alkyl groups, examples of which include Stepan Company's Biosoft, and Pilot Chemical Company's Calsoft. Still further suitable surfactants are the alkyldiphenylether disulfonates (also called alkyldiphenyloxide disulfonates), such as those sold by Dow Chemical Company under the name "Dowfax," e.g., Dowfax 3B2. Still other potentially suitable anionic surfactants include alkali metal alkyl sulfates such as Conco Sulfate WR, sold by Continental Chemical Company, which has an alkyl group of about 16 carbon atoms; and secondary alkane sulfonates such as Hostapur SAS, manufactured by Farbwerke Hoechst AG. Hydrotropes, on the other hand, are dispersants which do not form a critical micelle concentration (CMC) in water (See Colbom et al, U.S. Pat. No. 4,863,633, column 8, line 20 through column 10, line 22, incorporated herein by reference). These hydrotropes may interact with some of the bleach stable surfactants bearing at least one nitrogen atom to form thickened, viscoelastic formulations, although it is again emphasized that the thickening phenomenon is not critical to the enhanced brightness retention of the invention. The hydrotropes are preferably selected from short chain alkylarylsulfonates, salts of benzoic acid, benzoic acid derivatives (such as chlorobenzoic acid), and mixtures thereof. As used herein, aryl includes benzene, naphthalene, xylene, cumene and similar aromatic nuclei. These aryl groups can be substituted with one or more substituents known to those skilled in the art, e.g., halo (chloro, bromo, iodo, fluoro), nitro, or $C_{1-4}$ alkyl or alkoxy. Most preferred is sodium xylene sulfonate (such as Stepanate SXS, available from Stepan Company). The bleach stable anionic surfactant and/or hydrotrope should be present in a ratio with the bleach stable surfactant with at least one nitrogen atom (described above in 2.) between about 10:1 to about 1:10. Suitable levels of a secondary surfactant and/or hydrotrope, when employed, are similar to the levels employed for a first surfactant, as referenced herein.

Sequestrant/Chelant

Optionally, sequestering agents may be suitable for use in the inventive disinfectant articles. Sequestering agents are selected from the group consisting of metal chelators, metal sequestrants and ion exchange materials known in the art. Preferably, metal chelators and metal sequestrants are selected from the group consisting of the alkali and alkaline earth salts of the phosphates, phosphonates, borates, silicates, polyfunctionally-substituted aromatic chelating agents, ethylenediamine tetra-acetate (EDTA) and ethylenediamine —N,N'-disuccinic acids, or mixtures thereof. Preferred sequestering agents are the silicates and ethylenediamine tetra-acetate.

Polyfunctionally-substituted aromatic chelating agents may also be useful in the bleaching compositions herein. See U.S. Pat. No. 3,812,044, issued May 21, 1974, to Connor et al. Preferred compounds of this type in acid form are dihydroxydisulfobenzenes such as 1,2-dihydroxy-3,-5-disulfobenzene. A preferred biodegradable chelating agent for use herein is ethylene diamine N,N'-disuccinic acid, or alkali metal, or alkaline earth, ammonium or substituted ammonium salts thereof or mixtures thereof.

Sequestering agents are also selected from the group consisting of polyacrylic acid, a polyacrylic acid derivative, or a copolymer of acrylic acid or methacrylic acid and a comonomer, which is maleic acid or maleic anhydride. By "polyacrylic acid derivative" is meant copolymers derived from acrylic monomers and non-acrylic monomers. Acrylic monomers generally refer to esters of acrylic acid and methacrylic acid as well as those of other α-substituted acrylic acids (e.g., α-chloroacrylic, and α-ethylacrylic acids). Preferred acrylic monomers include, for example, acrylic acid and methacrylic acid. Suitable non-acrylic acid monomers include, for example, ethylene and propylene.

Other suitable polycarboxylate sequestering agents include, for example, polymethacrylate (DAXAD 30,35, 37™ from W. R. Grace & Co. and ALCOSPERSE 124™ from ALCO Chemical), acrylic acid/methacrylic acid (SOKOLAN CP 135™ from BASF Corp.), an oxidized ethylene/acrylic acid, carboxylated vinyl acetate (DARATAK 78L™ from W. R. Grace), vinyl acetate/crotonic acid (LUVISET CA66™ from BASF Corp.), vinyl acetate/vinyl propionate/crontonic (LUVISET CAP™ by BASF Corp.), vinyl acetate/vinyl neodecanoate/crontonic acid (Resyn 28-2930(by National Starch Co.), vinyl acetate/methacryloxy 1-benzophenone/crontonic acid (RESYN 28-3307™ from National Starch Co.), acrylic acid/methylethyl acrylate, ethylene/maleic acid (EMA™ from Monsanto Co.), poly(isobutylene/maleic acid) (DAXAD 31 ™ from W. R. Grace & Co.), maleic acid/vinyl acetate (LYTRON X 886™ from Monsanto Co.), poly(methyl vinyl ether/maleic acid) (SOKALAN CP2™ from BASF Corp.), poly(styrene/maleic anhydride) and mixtures thereof. Preferably the average molecular weight of the polycarboxylate polymer sequestering agent is between about 500 to 500,000 daltons and preferably ranges from about 1,000 to about 200,000 daltons, more preferably from about 3,000 to about 70,000 daltons.

Most preferably the sequestering agent is selected from polyacrylic acid, a polyacrylic acid derivative, a copolymer of acrylic acid or methacrylic acid and a comonomer, which is maleic acid or maleic anhydride and mixtures thereof.

Other Adjuncts

The disinfectant composition of the present invention may optionally be formulated to include further adjuncts, for example, thickening agents, rheology modifiers, fragrances, coloring agents, pigments (e.g., ultramarine blue), bleach-stable dyes (e.g., anthraquinone dyes), whiteners, including the optional surfactants, solvents, chelating agents and builders, which enhance performance, stability or aesthetic appeal of the composition. Generally, such adjuncts may be added in relatively low amounts, e.g., each from about 0.001 to about 5.0 weight percent of the composition. By way of example, a fragrance such as a fragrance commercially available from International Flavors and Fragrance, Inc., may be included in the inventive composition in an amount from about 0.01 to about 0.5 weight percent of the composition. Dyes and pigments may be included in small amounts, ultramarine blue (UMB) and copper phthalocyanines being examples of widely used pigments, which may be incorporated in the composition of the present invention.

Solvents may also be added to the inventive compositions to enhance cleaning and/or disinfectant efficacy of the compositions. For example, certain less water soluble or dispersible organic solvents, some of which are advantageously stable in the presence of hypochlorite bleach, may be included. These bleach-stable solvents include those commonly used as constituents of proprietary fragrance blends, such as terpenes and essential oils, and their respective derivatives.

The terpene derivatives suitable for the present invention include terpene hydrocarbons with a functional group. Effective terpenes with a functional group include, but are not limited to, alcohols, ethers, esters, aldehydes and ketones. Representative examples of each of the above-mentioned terpenes with a functional group include, but are not limited, to the following: (1) terpene alcohols, including, for example, verbenol, transpinocarveol, cis-2-pinanol, nopol, iso-borneol, carbeol, piperitol, thymol, alpha-terpineol, terpinen-4-ol, menthol, 1,8-terpin, dihydroterpineol, nerol, geraniol, linalool, citronellol, hydroxycitronellol, 3,7-dimethyl octanol, dihydromyrcenol, beta-terpineol, tetrahydro-alloocimenol and perillalcohol; (2) terpene ethers and esters, including, for example, 1,8-cineole, 1,4-cineole, iso-bornyl methylether, rose pyran, alpha-terpinyl methyl ether, menthofuran, trans-anethole, methyl chavicol, allocimene diepoxide, limonene mono-epoxide, iso-bornyl acetate, nopyl acetate, alpha-terpinyl acetate, linalyl acetate, geranyl acetate, citronellyl acetate, dihydro-terpinyl acetate and neryl acetate; and (3) terpene aldehydes and ketones, including, for example, myrtenal, campholenic aldehyde, perillaldehyde, citronellal, citral, hydroxy citronellal, camphor, verbenone, carvenone, dihydrocarvone, carvone, piperitone, menthone, geranyl acetone, pseudo-ionone, alpha-ionone, beta-ionone, iso-pseudo-methyl ionone, normal-pseudo-methyl ionone, iso-methyl ionone and normal-methyl ionone. Terpene hydrocarbons with functional groups which appear suitable for use in the present invention are discussed in substantially greater detail by Simonsen and Ross, The Terpenes, Volumes I-V, Cambridge University Press, $2^{nd}$ Ed., 1947, which is incorporated herein in entirety by this reference. See also, commonly assigned U.S. Pat. No. 5,279,758, issued to Choy on Jan. 18, 1994, which is incorporated herein in entirety by this reference.

Packaging Materials and Packaging Means

Suitable packaging materials may be provided by a variety of sources, and include all suitable materials that are hypohalite stable, in that they undergo no significant degradation, that is no significant chemical or physical change in structure, properties or form, owing to contact with the hypohalite compositions employed in the present invention. Suitable packaging materials include those materials common to the art.

Packaging means includes means for individually packaging the disinfectant wipes of the invention and means for bulk packaging one or more disinfectant wipes, or one or more individually packaged disinfecting articles. Such means includes those common to the art, such as tear open packets containing one or more individual disinfectant wipes and bulk dispensers such as canisters, tubs and containers that dispense one disinfectant wipe at a time and further feature suitable means to reseal the bulk dispenser between uses to preserve the integrity of the disinfecting articles. One example is a cylindrical canister dispenser that hosts a roll of individual wipes, separated by perforations to permit the tearing off of individual wipes for use. Such dispenser is conveniently gripped by the user and held in position while the user removes a wipe. Preferred are dispensers featuring a resealable dispensing cap and orifice (See, e.g., Chong, U.S. Pat. No. 6,554,156, of common assignment and incorporated herein by reference thereto) that dispenses individual wipes from a roll and retains the next wipe in a ready-to-dispense position, yet allows sealing of the dispensing cap to close the container against the environment when not in use. A further example, within the scope of the present invention, is to package individual wipes in a non-linked manner, in a dispenser permitting their removal one at a time—as is the case with many diaper wipe wipe/dispenser combinations known in the art.

Methods for Determining the Desired Properties

Samples of the inventive disinfectant articles and those of commercially available bleach containing wipes were evaluated for activity using oxidation/reduction titration methods known to those in the art.

To assess the level of available disinfectant, the amount of available halogen oxidant on the disinfectant articles were determined by placing about 2 to 3 gram samples of the disinfecting wipe into about 50 milliliters of distilled water, followed by addition of about 10 milliliters of a 10 weight/weight percent solution of potassium iodide and addition of about 10 milliliters of a 10 volume percent solution of sulfuric acid, the resulting mixture being well stirred. The resulting purple solution, whose color is the result of oxidation of free iodine ion (1) to molecular iodine ($I_2$), was then volumetrically titrated to an essentially colorless endpoint by addition of standardized 0.1 Molar sodium thiosulfate ($Na_2S_2O_3$) titrant. Calculations then express the result as percent of available active molecular chlorine ($Cl_2$), that is to say assigning two equivalents per mole of titrated hypohalite oxidant. Stability results are then expressed by repeated assays over time using identically prepared samples resulting from the same disinfectant solution and absorbent material, normalized to 100 percent representative of the starting available chlorine measured initially. This method allows fairly accurate assessment of the total amount of disinfectant absorbed onto their respective associated absorbent carrier materials.

EXAMPLES

Representative disinfecting compositions suitable for use on the disinfecting articles of the present invention are found in Table 1. Compositions are readily prepared by combining the ingredients in any order. Typically, addition of buffer/electrolyte materials is done in whole, if not in part, after addition of most other ingredients except water, to provide greater control and adjustment of the final composition pH.

Example A

The following disinfecting article, corresponding to Example A in Table 2, was prepared by dosing 2.75 grams of an aqueous solution containing about 0.55 weight % sodium hypochlorite, 0.05 weight % sodium lauryl sulfate and 0.32 weight % sodium hydroxide, per gram weight of a dry non-woven substrate from Polymer Group, Inc, designated 2006N, being a 100% spunlace polyester absorbent material capable of completely absorbing the applied solution without dripping.

Example B

Example B was prepared by dosing about 3.5 grams of the same composition employed in Example A, per gram weight of the same polyester material. In both Examples A and B, the absorbent material has an approximate basis weight of about 68 grams per square meter ($gm^{-2}$), and a corresponding rectangle of the material having dimensions of approximately 7 inches by 8 inches was used to prepare the disinfecting article.

Example C through H

Examples C through H were prepared in a similar fashion and using the same disinfectant solution as employed in Examples A and B, however, varying amounts of the solution were applied as required to achieve the gram/gram loading ratios as indicated in Table 2 using the corresponding absorbent materials as substrates as indicated in Table 2.

Comparative Examples I through L

Comparative Example I through L were prepared in a similar fashion and using the same disinfectant solution as employed in Examples A and B, however, varying amounts of the solution were applied as required to achieve the gram/gram loading ratios as indicated in Table 2. It should be noted that the absorbent material employed in Comparative Examples I and J is a commercially available 100% spunbond polypropylene available from Rockline, having a basis weight of about 44 $gm^{-2}$. Absorbent material employed in Comparative Examples K and L is a commercially available 100% spunbond polypropylene from Kimberly-Clarke, having a basis weight of about 34 $gm^{-2}$. The disinfecting articles were prepared by using the corresponding absorbent materials as substrates as indicated in Table 2.

Comparative Commercial Example

DISPATCH® Hospital Cleaner Disinfectant with Bleach pre-moistened towellete, available from Caltech Industries, was also evaluated for purposes of comparing versus the disinfectant articles of the current invention. It should be noted that the absorbent material employed in the DISPATCH towellete was identified as being an unmodified polypropylene polymer, a similar polymer as employed in Comparative Examples I through L above. The advantages of the present invention may clearly be seen by comparing the Examples of the present invention with the comparative examples and a leading commercially available disinfecting wipe.

Table 2 presents the stability of disinfectant articles prepared using a variety of selected polymer substrates, wherein examples A through H represent substrates used for the disinfectant absorbent carrier materials selected according to the requirements of the present invention. Comparative examples I through L employ the same aqueous disinfectant compositions as used in preparing example A, but employ substrates commonly used in commercial examples representative of the current state of the art, such as the DISPATCH® Hospital Cleaner Disinfectant with Bleach pre-moistened towellete, available from Caltech Industries. All examples prepared using the substrates of the present invention show improved stability and maintenance of an acceptable level of active disinfectant, even after test storage conditions chosen to represent accelerated ageing conditions.

Figure 1:
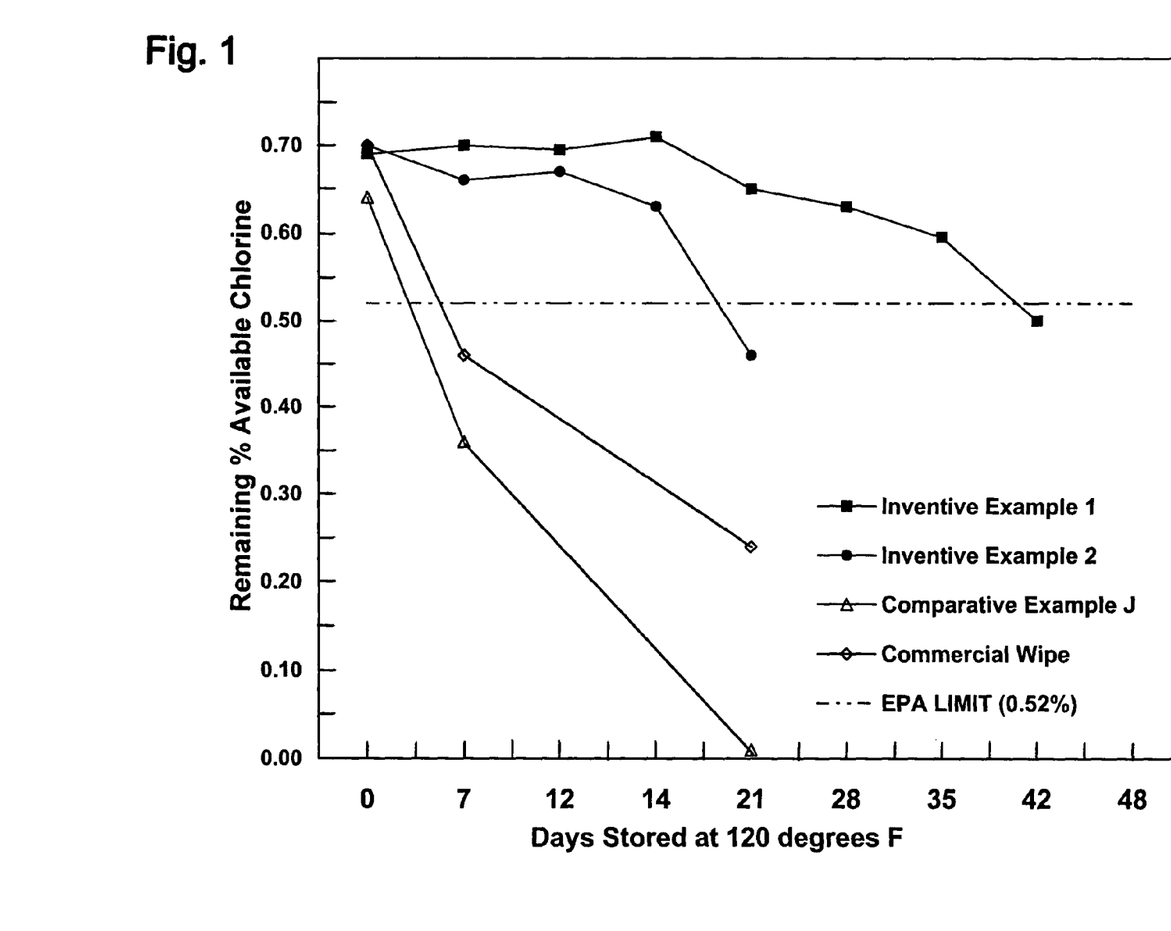
FIG. 1 Graph of remaining available chlorine on absorbent substrates under accelerated storage test conditions.

The advantages of the present invention are also graphically presented in FIG. 1. In FIG. 1, Inventive Example I and Inventive Example 2 are disinfectant articles prepared using absorbent carrier materials selected according the requirements of the present invention. Comparative examples J and a commercial wipe (the Dispatch disinfectant wipe) are also shown with the results of accelerating ageing of representative samples for an extended time at a temperature of 120 degrees Fahrenheit to simulate the effects of extended storage. Also shown in FIG. 1 is the acceptable lower available chlorine limit (EPA limit 0.52%) suggested by the United States Environmental Protection Agency (US-EPA) for a disinfecting bleach wipe for purposes of registration for use on food contact and other surfaces. The advantages of disinfecting articles of the present invention are clearly seen over the current state of art in FIG. 1 in providing a disinfectant article with improved stability and the extended disinfect efficacy associated with said improved stability, even after prolonged storage under adverse storage times and temperatures.

TABLE 1

Aqueous hypohalite compositions

| Ingredient | Composition # | | | | | |
|---|---|---|---|---|---|---|
| | 1 | 2 | 3 | 4 | 5 | 6 |
| Water (1) | 98.90 | 99.055 | 98.73 | 99.00 | 98.11 | 97.55 |
| Sodium hypochlorite (2) | 0.70 | 0.70 | 0.55 | 0.55 | 1.50 | 1.84 |
| Sodium hydroxide (3) | 0.10 | 0.15 | 0.32 | 0.15 | 0.10 | 0.32 |
| Surfactant A (4) | 0.05 | — | — | — | — | — |
| Surfactant B (5) | — | 0.05 | — | — | — | 0.2 |
| Surfactant C (6) | — | — | 0.05 | 0.05 | 0.20 | — |
| Fragrance (7) | 0.03 | 0.03 | 0.03 | 0.03 | 0.04 | 0.04 |
| Chelant (8) | 0.22 | 0.015 | 0.32 | 0.22 | 0.05 | 0.05 |

(1) Distilled or deionized water
(2) Source is plant produced sodium hypochlorite diluted from high strength stock
(3) Product of J. T. Baker
(4) Sodium xylene sulfonate, anionic hydrotrope.
(5) Lauryl amine oxide surfactant, product of Stepan Company
(6) Sodium lauryl sulfate, anionic surfactant, product of Stepan Company
(7) Perfume composition from Quest corporation
(8) Sodium silicate solution from PQ Corporation

TABLE 2

Stability of Disinfectant Articles

| System (1) | Substrate (2) | Basis Weight (3) | Loading Ratio (4) | % Active Initial (5) | % Active 1 Day (6) @ 120 F | % Active 5 Days @ 120 F | % Active 11 Days @ 120 F |
|---|---|---|---|---|---|---|---|
| Inventive A | PE2006N | 68 | 2.75 | 100 | 98.6 | 94.3 | 80.0 |
| Inventive B | PE2006N | 68 | 3.5 | 100 | 100 | 95.7 | 85.7 |
| Inventive C | PEM017 | 58 | 2.75 | 100 | 100 | 95.7 | 75.7 |
| Inventive D | PEM017 | 58 | 3.5 | 100 | 100 | 97.1 | 81.4 |
| Inventive E | HPE8010 | 45 | 2.75 | 100 | 100 | 91.4 | 75.7 |
| Inventive F | HPE8010 | 45 | 3.5 | 100 | 98.6 | 95.7 | 81.4 |
| Inventive G | HPE8005 | 68 | 2.75 | 100 | —(7) | 87.1 | 61.4 |
| Inventive H | HPE8005 | 68 | 3.5 | 100 | —(7) | 88.6 | 70.0 |
| Comparative I | PP Donut | 44 | 2.75 | 100 | 97.1 | 54.3 | trace (8) |
| Comparative J | PP Donut | 44 | 3.5 | 100 | 95.7 | 44.3 | trace (8) |
| Comparative K | PP 1.2 | 34 | 2.75 | 100 | 100 | 95.7 | trace (8) |
| Comparative L | PP 1.2 | 34 | 3.5 | 100 | 100 | 97.1 | trace (8) |
| Dispatch (9) | PP | — | ~5 | 100 (10) mea. | 91.4 | 84.3 | trace (8) |
| Neat solution A-L (11) | None (12) | — | — | 100 | — | — | 54.3 |

(1) System is absorbent substrate loaded at loading ratio with neat sodium hypochlorite solution (Composition 1 detailed in Table 1)
(2) Substrates include 100% polyester (PE 2006N, PE M017) from Polymer Group Inc., 100% polyester (PE 8010) from Dupont, hydrophilically modified polyester (HPE 8005H) from Dupont, 100% polypropylene (PP donut) from Rockline, Inc. and 100% polypropylene (PP 1.2) from Kimberly-Clarke Corporation, each having basis weights as indicated in Column 3. Substrate size tested is 7" × 8" size for Inventive examples A–H and 6" × 6.75" for comparative examples I–L. Dispatch Wipe is analyzed as being 100% polypropylene (PP).
(3) Basis weight expressed in gram/m² (gm⁻²)
(4) Loading ratio expressed in (unit less) ratio of applied composition weight/dry absorbent weight
(5) % Active is the available chlorine measured via titration method described in the specification herein. Measured immediately following loading, unless stated otherwise.
(6) % Active is the remaining available chlorine at indicated time, determined by assaying replicates stored in sealed cylindrical container away from light under constant temperature conditions at 120° F., unless otherwise noted.
(7) Missed data point
(8) Lower limit of detection corresponds to about 0.01 wt % active chlorine, or about 1.4% remaining activity, recorded as "trace."
(9) DISPATCH ® Hospital Cleaner Disinfectant with Bleach pre-moistened towelette, available from Caltech Industries. Substrate was identified as unmodified polypropylene polymer. Wipe size measured to be 7" × 8".
(10) Measured immediately following opening of replicate representative Dispatch towelletes randomly selected from box lot.
(11) Neat aqueous liquid disinfectant composition used for dosing absorbent carriers, corresponding to Example composition # 1 detailed in Table 1.
(12) Neat aqueous liquid stored in similar liquid tight canister as where the disinfectant articles under identical storage conditions to serve as reference control.

Disinfectancy Contact Time

Table 3 presents disinfectancy tests results of the inventive disinfectant wipes used against three microorganisms, Staphylococcus aureus, Salmonella chloreaesuis and Pseudomonas aeruginosa, present on contaminated hard surfaces with 5% soil load, following test methodology suggested by the United States Environmental Protection Agency (US-EPA) to establish disinfectant efficacy of wipes. The results clearly indicate the superiority of the disinfectant articles of the present invention in achieving disinfectancy, that is 100% effective destruction of viable microorganisms, on soiled hard surfaces within 30 second exposure times, compared to the commercial Dispatch Wipes product that requires I full minute for disinfectancy.

TABLE 3

Minimum Contact Time for Disinfectant Efficacy against Microorganism

| Microorganism (1) | Dispatch Wipe (2) | Inventive Disinfectant Wipe (3) |
|---|---|---|
| Staphylococcus aureus | 1 min. | 30 sec |
| Salmonella chloreaesuis | 1 min. | 30 sec |
| Pseudomonas aeruginosa | 1 min. | 30 sec |

(1) Selected microorganisms suggested by the United States Environmental Protection Agency for disinfectant spray testing on hard non-porous surface with 5% soil load
(2) DISPATCH ® Hospital Cleaner Disinfectant with Bleach pre-moistened towellete, available from Caltech Industries. Label states a minimum level of 0.52 weight % active as sodium hypochorite. Minimum contact times effective for target organisms as stated on product master label.
(3) Inventive disinfectant wipe corresponding to Composition # 3 (Table 1) with a 0.55 weight % sodium hypochlorite loaded onto a 100% polyester substrate.

What is claimed is:

1. A disinfecting system comprising:
   a. at least one disinfectant substrate comprising:
      i. an aqueous hypohalite releasing composition, and
      ii an absorbent carrier; and
   b. a packaging system dispensibly housing one or more disinfectant substrates,
   c. wherein said disinfecting article maintains the at least 25% of the starting concentration of hypohalite after 11 days at 120° F.

2. The disinfecting article of claim 1, wherein said absorbent carrier is impregnated with a disinfecting amount of said aqueous hypohalite releasing composition.

3. The disinfecting article of claim 1, wherein said absorbent carrier comprises a synthetic polymer substrate selected from the group consisting of polyester, polyethylene, hydrophobically modified polyester, hydrophilically modified polyester, and mixtures thereof.

4. The disinfecting article of claim 1, wherein said absorbent carrier further comprises a substantially attached layer of a liquid impervious barrier, said barrier substantially attached to at least one portion of the absorbent carrier so as to provide a liquid impervious barrier between the absorbent carrier and a gripping means, wherein said liquid impervious barrier substantially prevents contact of said aqueous hypohalite releasing composition with said gripping means.

5. The disinfecting article of claim 1, wherein said absorbent carrier attaches to a cleaning implement.

6. The disinfecting article of claim 1, wherein said aqueous hypohalite releasing composition comprises:
   a. an alkali metal hypohalite,
   b. a source of alkalinity, and
   c. optionally, one or more hypohalite stable adjuncts; selected from the group consisting of surfactants, hydrotropes, stabilizers, sequestrants, thickeners, rheology modifiers, tensides, phase transfer agents, wetting agents, anti-foam agents, fragrances, colorants, pigments, dyes and the like, and mixtures thereof.

7. The disinfecting article of claim 6, wherein the alkali metal hypohalite is sodium hypochlorite, and wherein the source of alkalinity is selected from the group consisting of sodium hydroxide, and potassium hydroxide and mixtures thereof.

8. The disinfecting article of claim 6, wherein the alkali metal hypohalite is sodium hypochlorite, and wherein the source of alkalinity is selected from the group consisting of borates, polyphosphates, pyrophosphates, triphosphates, tetraphosphates, silicates, metasilicates, polysilicates, carbonates, and mixtures thereof.

9. The disinfecting article of claim 1, wherein said packaging system is adapted to securely hold a single or multiple number of disinfecting articles, and wherein said packaging system comprises a substantially liquid impervious sealable package means.

10. The disinfecting article of claim 1, wherein said packaging system is adapted to securely hold a single or multiple number of disinfecting articles, and wherein said packaging system comprises a substantially gas impervious sealable package means.

11. The disinfecting article of claim 1, wherein said packaging system comprises a substantially liquid impervious sealable packaging system selected from the group consisting of a pouch, a container, a tub, a cylindrical package, and combinations thereof, and wherein said packaging system provides for the storage of disinfecting articles selected from the group consisting of a single and a multiple number of articles.

12. A method of disinfecting hard surfaces comprising treating the hard surface with a disinfecting article comprising:
   a. an aqueous hypohalite releasing composition,
   b. an absorbent carrier, and
   c. wherein said disinfecting article maintains at least 25% of the starting concentration of the hypohalite after 11 days at 120° F.

13. The method claim 12, wherein said absorbent carrier is impregnated with a disinfecting amount of said aqueous hypohalite releasing composition.

14. The method claim 12, wherein said absorbent carrier comprises a synthetic polymer substrate selected from the group consisting of polyester, polyethylene, hydrophobically modified polyester, hydrophilically modified polyester, and mixtures thereof.

15. The method claim 12, wherein said absorbent carrier further comprises a substantially attached layer of a liquid impervious barrier, said barrier substantially attached to at least one portion of the absorbent carrier so as to provide a liquid impervious barrier between the absorbent carrier and a gripping means, wherein said liquid impervious barrier substantially prevents contact of said aqueous hypohalite releasing composition with said gripping means.

16. The method of claim 12, wherein said absorbent carrier attaches to a cleaning implement.

17. The method of claim 12, wherein the aqueous hypohalite releasing compositions comprises:
   a. an alkali metal hypohalite,
   b. a source of alkalinity, and c. optionally, one or more hypohalite stable adjuncts, selected from the group consisting of surfactants, hydrotropes, stabilizers, sequestrants, thickeners, rheology modifiers, tensides, phase transfer agents, wetting agents, anti-foam agents, fragrances, colorants, pigments, dyes and the like, and mixtures thereof.

18. The method of of claim 17, wherein the alkali metal hypohalite is sodium hypochlorite, and wherein the source of alkalinity is selected from the group consisting of sodium hydroxide, potassium hydroxide, and mixtures thereof.

19. The method of claim 17, wherein the alkali metal hypohalite is sodium hypochlorite, and wherein the source of alkalinity is selected from the group consisting of borates, polyphosphates, pyrophosphates, triphosphates, tetraphosphates, silicates, metasilicates, polysilicates, carbonates, and mixtures thereof.

20. The method of claim 12, wherein said packaging system is adapted to securely hold a single or multiple number of disinfecting articles, and wherein said packaging system comprises a substantially liquid impervious sealable package means.

21. The method of of claim 12, wherein said packaging system is adapted to securely hold a single or multiple number of disinfecting articles, and wherein said packaging system comprises a substantially gas impervious sealable package means.

22. A The method of claim 12, wherein said packaging system comprises a substantially liquid impervious sealable packaging system selected from the group consisting of a pouch, a container, a tub, a cylindrical package, and combinations thereof, and wherein said packaging system provides for the storage of a single or multiple number of disinfeeting articles.

23. A hypochlorite disinfecting wipe providesing disinfection against Staphylococcus aureus within 30 seconds on surfaces selected from the group consisting of countertops, floors, beds, walls, doorknobs, toilet seats, and combinations thereof.

24. The hypochlorite disinfecting wipe of claim 23, wherein said wipe attaches to a cleaning implement.

25. A method oftreating a surface comprising the step of treating said surface with a hypochiorite wipe providing disinfection against Staphylococcus aureus within 30 seconds, wherein said surface is selected from the group consisting of countertops, floors, beds, walls, doorknobs, toilet seats, and combinations thereof.

26. The method of claim 12, wherein said concentration of hypohalite is measured with said disinfecting article stored in a container sealed from evaporation.

* * * * *